US012782480B2

(12) United States Patent
Popescu

(10) Patent No.: US 12,782,480 B2
(45) Date of Patent: Nov. 3, 2026

(54) RECONFIGURABLE LOCAL COIL, DEVICE FOR RECONFIGURING AND METHOD FOR OPERATION

(71) Applicant: Siemens Healthineers AG, Forchheim (DE)

(72) Inventor: Stefan Popescu, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/888,675

(22) Filed: Sep. 18, 2024

(65) Prior Publication Data

US 2025/0093445 A1 Mar. 20, 2025

(30) Foreign Application Priority Data

Sep. 20, 2023 (DE) ..................... 10 2023 209 136.4

(51) Int. Cl.

*G01R 33/385* (2006.01)
*A61B 5/055* (2006.01)
*G01R 33/56* (2006.01)

(52) U.S. Cl.

CPC .......... *G01R 33/3852* (2013.01); *A61B 5/055* (2013.01); *G01R 33/5608* (2013.01)

(58) Field of Classification Search

CPC .. G01R 33/3852; G01R 33/5608; A61B 5/055
See application file for complete search history.

(56) References Cited

U.S. PATENT DOCUMENTS 4,768,008 A * 8/1988 Purcell ............... G01R 33/3815 324/318
4,879,515 A * 11/1989 Roemer ............... G01R 33/422 324/318
5,680,046 A * 10/1997 Frederick ............ G01R 33/422 324/318

(Continued)

FOREIGN PATENT DOCUMENTS

WO 02059059 A2 8/2002
WO 2017007365 A1 1/2017

(Continued)

OTHER PUBLICATIONS

Chi Zhonghai et al:; "Adaptive cylindrical wireless metasurfaces in clinical magnetic resonance imaging"; Advanced Materials; 2021, vol. 33.; Nr. 40; pp. 2102469.

(Continued)

*Primary Examiner* — Dixomara Vargas
(74) *Attorney, Agent, or Firm* — Lempia Summerfield Katz LLC

(57) ABSTRACT

A device having a field control material for arrangement between a local coil and a patient and a local coil, a magnetic resonance tomography system having the local coil and a method for operating the magnetic resonance tomography system. The device has a control input and the field control material is configured to modify the spatial propagation of an electrical and/or magnetic alternating field as a function of a control signal at the control input. The magnetic resonance tomography system captures images with different settings of the field control material.

10 Claims, 6 Drawing Sheets

(56) References Cited

U.S. PATENT DOCUMENTS 5,729,141 A * 3/1998 Hass .................... G01R 33/385 324/318
5,986,531 A * 11/1999 Carrozzi .............. G01R 33/422 324/318
7,852,176 B2 12/2010 Chang
8,319,495 B1 * 11/2012 Zhu .................... G01R 33/5612 324/309
10,324,152 B2 6/2019 Zhang
10,871,532 B2 12/2020 Popescu
2002/0120191 A1 * 8/2002 Boskamp ............. G01R 33/422 600/422
2002/0149367 A1 * 10/2002 Boskamp ............... G01R 33/34 324/309
2002/0165080 A1 11/2002 Sengupta
2002/0165447 A1 * 11/2002 Boskamp ......... G01R 33/34046 600/422
2003/0206017 A1 * 11/2003 Boskamp ............. G01R 33/385 324/309
2006/0001425 A1 * 1/2006 Weyers ............ G01R 33/34046 324/318
2006/0012369 A1 * 1/2006 Neufeld ........... G01R 33/34046 324/318
2008/0164876 A1 * 7/2008 Sakakura ........... G01R 33/3873 324/318
2009/0299170 A1 * 12/2009 Gebhardt .............. G01T 1/1603 600/411
2010/0219347 A1 * 9/2010 Schulz .................. G01T 1/1603 250/363.04
2012/0068710 A1 * 3/2012 Biber ................... G01R 33/422 324/322
2012/0229141 A1 * 9/2012 Brown ................. G01R 33/341 324/322
2013/0207659 A1 * 8/2013 Ham .................... G01R 33/422 324/322
2014/0361769 A1 * 12/2014 Hardie ............... G01R 33/3692 324/322
2015/0008924 A1 * 1/2015 Van Helvoort .... G01R 33/4215 324/318
2015/0212174 A1 * 7/2015 Brown ............. G01R 33/56518 324/322
2016/0256712 A1 * 9/2016 Vahala ................. A61N 5/1039
2016/0327619 A1 * 11/2016 Kim ..................... G01R 33/422
2018/0188339 A1 7/2018 Slobozhanyuk
2021/0048493 A1 * 2/2021 Scheffler ............ G01R 33/3671
2021/0100475 A1 * 4/2021 Zhang .................... A61B 5/055
2021/0103017 A1 * 4/2021 Dyvorne ................ A61B 5/055
2022/0095944 A1 3/2022 Zhang
2022/0206089 A1 * 6/2022 Zhao .................. G01R 33/3642
2022/0291311 A1 * 9/2022 Rizza ...................... G01R 33/36
2022/0413070 A1 12/2022 Saha
2023/0059453 A1 * 2/2023 Kondo ............... G01R 33/4835

FOREIGN PATENT DOCUMENTS

WO 2021156613 A1 8/2021
WO 2021242135 A1 12/2021

OTHER PUBLICATIONS

Lippke Marius et al:; "Investigation of a Digitally-Reconfigurable Metasurface for Magnetic Resonance Imaging"; Proceedings of the 52nd European Microwave Conference (EuMC).; IEEE, 2022; pp. 668-671.

Wang, Hanwei et al:; "On-demand field shaping for enhanced magnetic resonance imaging using an ultrathin reconfigurable metasurface".; View, 2021; vol. 2., Nr. 3, pp. 20200099.

* cited by examiner

RECONFIGURABLE LOCAL COIL, DEVICE FOR RECONFIGURING AND METHOD FOR OPERATION

CROSS REFERENCE TO RELATED APPLICATIONS

This application claims the benefit DE 10 2023 209 136.4 filed on Sep. 20, 2023, which is hereby incorporated by reference in its entirety.

FIELD

Embodiments relate to a device including a field control material for arrangement between a local coil and a patient, and a local coil and a magnetic resonance tomography system including the device. The device includes a control input for modification of electrical and/or magnetic fields by the field control material.

BACKGROUND

Magnetic resonance tomography systems are imaging devices which, to map an object under examination, orient nuclear spins of the object under examination using a strong external magnetic field and excite them for precession around this alignment by an alternating magnetic field. The precession or return of the spins from this excited state into a state with less energy in turn generates a magnetic alternating field in response, that is received via antennas.

With the help of magnetic gradient fields, position encoding is impressed on the signals, which subsequently enables the received signal to be assigned to a volume element. The received signal is then evaluated and a three-dimensional imaging representation of the object under examination is provided. For the receipt of the signals, use is made of local receiving antennas, known as local coils, that in order to achieve a better signal-to-noise ratio are arranged directly on the object under examination.

Compared to other modalities, imaging using magnetic resonance tomography systems is relatively slow, since because of the weak signals of the nuclear spins, due to the high temperature and thus the small deviation of the nuclear spins from thermal equilibrium, the signal-to-noise ratio is low and long integration times are necessary.

This may be remedied by scanning several slices in parallel. For this, the signals from different volumes must be received by separate antenna coils in order to enable a parallel evaluation without crosstalk. The smaller the antenna coils are, the more volumes may be captured in parallel. However, the signal and thus the signal-to-noise ratio decreases again with the size of the coils, that requires longer integration.

Known from the publication U.S. Pat. No. 10,324,152 B2 is an arrangement including passive resonators that improves the signal-to-noise ratio of radio signals, emitted by an object under examination and received by the magnetic resonance tomography system.

BRIEF SUMMARY AND DESCRIPTION

The scope of the embodiments is defined solely by the appended claims and is not affected to any degree by the statements within this summary. The present embodiments may obviate one or more of the drawbacks or limitations in the related art. Independent of the grammatical term usage, individuals with male, female or other gender identities are included within the term.

Embodiments provide a device and a method to accelerate image capture with a magnetic resonance tomography system.

The device includes a field control material. The term field control material refers both to an artificially produced structure, that for electrical and/or magnetic alternating fields includes, at least for a predetermined frequency of the alternating fields, propagation properties that differ from properties of natural, homogeneous materials. Such materials are also referred to as metamaterial. Metamaterials are known for example from the publication U.S. Pat. No. 10,324,152 B2.

The field control material may have controllable properties comparable to liquid crystals or other optically active media in the range of the radio frequencies and thus of the magnetic resonance signals. Materials whose dielectric constant or permeability depends on external parameters such as an external static electric field, pressure or other modifiable macroscopic variables would for example be conceivable. Such materials are known from the documents WO 2002059059 and U.S. Pat. No. 7,852,176.

The device is provided for arrangement between a local coil matrix and a patient. The device includes a planar configuration, i.e. the dimension of the device in the arrangement according to the application is greater in directions parallel to the surface of the patient and/or the local coil than in a direction perpendicular thereto. The device may be flexible or divided into segments that are flexibly connected to one another so that the device may mold itself to a surface of the patient.

The device further includes a control input. The field control material is configured, in response to a control signal via the control input, to modify a spatial propagation of an electrical and/or magnetic alternating field. In other words, the field control material may be brought by the control signal into at least two different states, in which an electrical and/or magnetic alternating field propagates differently through the field control material and thus results in different field strengths on the side of the field control material facing away from the field source for the at least two states. This applies both when transmitting, when the local coil as a transmitting antenna emits an excitation pulse into the patient, and when receiving, when magnetic alternating fields emitted by the nuclear spins are recorded by the antenna coil(s).

The different states of the field control material may for example be caused by electromagnetic resonance elements in the material, whose resonance behavior is modified by the control signal, for example a voltage. Different polarization states or mechanical configurations brought about by the control signal are also conceivable. Different embodiments are explained below.

The device makes it possible to modify the field characteristics and thus the spatial transmission and reception properties in a controlled manner in a local coil and thus to capture different volumes in a controlled manner, that makes the possibilities for image capture more variable and also enables acceleration, that is also explained in examples below. Homogenization of a field strength of an excitation pulse is thus also conceivable.

The local coil includes a local coil matrix with a plurality of antenna coils to capture magnetic resonance signals and/or to emit an excitation pulse. Furthermore, the local coil includes a device. The device is arranged on a surface of the local coil, such that when the local coil is arranged on a patient in accordance with the application the device is arranged on the surface of the patient. the device may also be protected by a casing, either by a separate casing or by the casing of the local coil, in other words the device may also be arranged inside the local coil.

The magnetic resonance tomography system includes a local coil with a device. The magnetic resonance tomography system further includes a controller that is in signal connection with the control input of the device. The signal connection may be electrical, but optical signal connections via fiber-optic conductors or hydraulic or pneumatic signal connections are also conceivable. If the device includes a plurality of segments made of field control material the signal connection may also have a plurality of channels to control the segments independently of one another. Also conceivable is a control unit or multiplexer that further distributes the channels as signals for the respective segment. the signal connection may also be wireless.

The controller of the magnetic resonance tomography system is configured to set the states of the field control material or of the segments as a function of a sequence. Various examples of how the local coil with the device and the magnetic resonance tomography system may improve image capture are specified for the subclaims.

The local coil and the magnetic resonance tomography system share the advantages of the device.

The method is executed on a magnetic resonance tomography system with a local coil and device. In a step of the magnetic resonance tomography system an excitation pulse is emitted by the radio-frequency unit. The radio-frequency pulse depends on the image capture sequence selected. The excitation pulse may be emitted via the local coil instead of via a body coil. One use of the device for decoupling the excitation pulse is specified below. In the simplest case, the field control material of the device is in a first state that is transparent for the electrical and/or magnetic alternating fields while the excitation pulse is being emitted.

In a further step of the method the controller of the magnetic resonance tomography system sets a second state of the field control material, in which the field strength of an incident electrical and/or magnetic wave front of an alternating field in a predetermined first volume is increased relative to the transparent state. In other words, in the second state of the field control material the propagation conditions of the magnetic resonance signals are modified, so that the antenna coil(s) captures signals from a predetermined volume.

In a further step the focused magnetic resonance signals are captured with the local coil and are forwarded to a receiver of the radio-frequency unit of the magnetic resonance tomography system for further evaluation.

In another step of the method, an image is reconstructed from the captured magnetic resonance signal, and is output to a user in another step.

The method provides an accelerated and/or improved image capture in the magnetic resonance tomography system, in that the sensitivity region is modified by the field control material.

In another form of embodiment of the method a $B1^+$ field map is initially provided. A $B1^+$ field map here refers to a map that indicates how strong an excitation of the nuclear spins of the object under examination is in the case of a predetermined excitation pulse emitted via the local coil in a predetermined state of the field control material at a plurality of locations in an image capture area (FoV) of the magnetic resonance tomography system. Such a $B1^+$ field map may for example be determined with a measurement or image capture using a homogeneous phantom with the predetermined excitation pulse in the predetermined state of the field control material. The B1+ field map may for example be determined in a calibration measurement and then stored in the controller of the magnetic resonance tomography system for future image captures. The B1+ field map may also be provided by convolving a local-coil-specific B1+ field map and a map for the magnetic resonance tomography system, that capture the influence of different positions of the local coil in the magnetic resonance tomography system, in order to generate a B1+ field map for different relative positions of the local coil without a new calibration measurement in each case.

In a further step a fourth state of the field control material is determined, that then during the emission of the predetermined excitation pulse homogenizes the excitation of the nuclear spins in the object under examination. The fourth state differs for example from the first state of the field control material, that is characterized in that the field control material in the first state is transparent and does not modify, for example does not homogenize, the propagation of the fields.

Homogenization is of particular importance if the variation possibilities for the predetermined excitation pulse are limited, for example because the number of transmission channels is limited to a small number, for example one channel, 2, 4 or fewer than 10 channels. Homogenization may be achieved by generating a dispersion or broader spatial distribution of the field in areas with a high field strength as explained below and by focusing in areas with a lower field strength. The fourth state may for example be determined using an optimization method, in which the deviation of the field strengths from a mean value is minimized in the image capture area or a subset thereof.

The further steps are or will be explained in greater detail in connection with another form of embodiment of the method. The fourth state of the field control material is set by the controller. The predetermined excitation pulse is then emitted by the radio-frequency unit, for example by the local coil. A magnetic resonance signal is then captured with the local coil. A reconstruction of an image is generated from the captured magnetic resonance signal and is output to a user.

By the field control material, a homogenization of the excitation of the nuclear spins and thus the image quality may be improved even in the case of a small number of transmission channels of the radio-frequency unit that are independent of one another.

In an embodiment, the field control material is configured to be transparent for the electrical and/or magnetic alternating field in a first state. Transparent is for example understood to mean that the propagation or the spatial characteristic of the electrical and/or magnetic alternating field remains unmodified from the field control material in the first state. In other words, the field strength is not modified by the field control material in the first transparent state or is only modified in a spatially homogeneous way outside the field control material, e.g. reduced to a small extent, for example attenuated by less than 3 dB or 1 dB.

In a second state the field control material raises the field strength of an incident electrical and/or magnetic wave front of an alternating field in a predetermined first volume relative to the transparent state. In other words, the field control material focuses the electrical and/or magnetic alternating field in the second state in a predetermined manner in a predetermined volume.

Changing the properties of the field control material permits the propagation condition of the fields to vary, for example in order when receiving to prefer a determined volume and when transmitting to prevent any hazard from field peaks.

In an embodiment the field control material includes a third state. The field control material is configured in this third state to raise the field strength of an incident electrical and/or magnetic wave front of an alternating field in a predetermined second volume relative to the transparent state. The second volume is different or disjunct from the first volume. In other words, besides the transparent state, that may for example be used for the excitation of the nuclear spins, a local coil matrix may, by the field control material, achieve at least two predetermined different sensitivity patterns on receipt of magnetic resonance signals.

These different sensitivity patterns may be used to independently scan different regions for acceleration through parallelization. An image capture using compressed sensing is also conceivable, in which the same volume is captured with different sensitivity patterns.

To this end, the field control material includes a plurality of predetermined states, each with different sensitivity patterns. This may be achieved for example in that the field control material includes a plurality of segments, whose at least two states may each be controlled independently of one another. The combination or permutation of the states then produces a corresponding plurality of overall states or sensitivity patterns.

In an embodiment of the device the predetermined first volume or second volume is a cone, a wedge or a slice parallel to a surface of the device. It is also conceivable for both the first volume and the second volume to have the same shape, for example in the form of slices or wedges, though these have a different position or orientation.

Cones, wedges or slices permit a spatial separation of the signals and thus an acceleration through parallelization.

In an embodiment of the local coil, the device includes a plurality of segments made of the field control material. The segments may be physically separate elements that are arranged adjoining one another on the local coil, in order to cover the surface facing the patient in whole or in part. However, it is also conceivable for the segments to be merely logically characterized in that the state or the properties of an entire segment are each influenced by a common control input. The control input may also be regarded as a logical control input, i.e. multiple segments are controlled independently of one another via a multiplexed physical control input. A segment is then defined as a region of the field control material that may be transferred into the different states via a logical control input independently of the other regions. For example, each segment may be transferred into a first state or a second state separately via the control input.

In each case at least one segment of an antenna coil lies opposite the local coil matrix and each segment is configured to be transferred into the first state or the second state separately via the control input. It is also conceivable for a plurality of segments to be assigned to an antenna coil in each case and to be arranged opposite.

Opposite means if a projection of the segment along a normal vector of a surface surrounded by the antenna loop comes to rest on the surface wholly or at least mostly, i.e. more than 50%. The field control material may for example be arranged on a support material of the antenna coil or on a casing of the antenna coil or local coil matrix.

The plurality of segments of the field control material permits a plurality of sensitivity patterns on receipt of the magnetic resonance signals and/or also on transmission of the excitation pulses, that advantageously permit a parallelization or image capture by compressed sensing. With a plurality of segments that lie opposite an individual antenna coil, it is also conceivable to enable adjustable beamforming or focusing and control of the direction of the maximum sensitivity of the antenna coil.

In an embodiment of the magnetic resonance tomography system the electrical and/or magnetic alternating field includes a frequency in a range of a Larmor frequency of nuclear spins to be mapped in the magnetic resonance tomography system. The Larmor frequency is defined by the magnetic moment of the spins to be mapped and the magnetic field provided by the magnetic resonance tomography system.

For example, in the case of field control materials such as metamaterials, that for example are provided by macroscopic resonance elements distributed across the metamaterial, the achievable frequency range for the states is limited. The precise definition of these effective frequencies by the Larmor frequency enables their effective use. In principle however it is also conceivable for other field control materials to cover wide frequency ranges.

In an embodiment of the method the controller sets the first state of the field control material in a step prior to the step of emitting the excitation pulse. In the first state the field control material is transparent for electrical and/or magnetic alternating fields, i.e. the field control material at most modifies a field strength and direction of the fields slightly, for example the direction of the field vectors by less than 30 degrees, 10 degrees or 5 degrees or the field strength by less than 6 dB, 3 dB or 1 dB.

Thanks to the transparent first state it is ensured during the excitation pulse that the field distribution remains unmodified and thus without any new field peaks that could pose a hazard to a patient.

In an embodiment of the method the step of the emission of the excitation pulse is repeated, in a step the third state of the field control material is set by the controller, and in a step in turn a magnetic resonance signal is captured. The third state differs from the second state for example in that the sensitivity patterns for an antenna coil change opposite or behind the field control material.

The sensitivity patterns modified by the third and if appropriate also by further states enable an image capture by compressed sensing.

DETAILED DESCRIPTION

Figure 1:
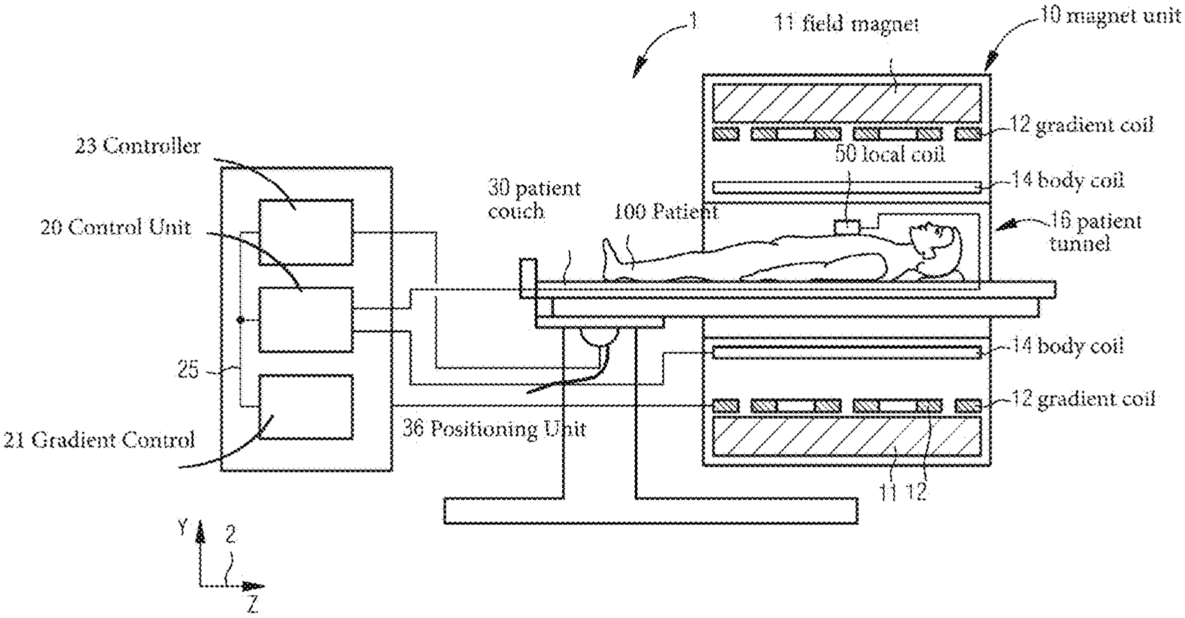
FIG. 1 depicts a schematic representation of a magnetic resonance tomography system according to an embodiment.

FIG. 1 depicts a schematic representation of an embodiment of a magnetic resonance tomography system 1.

The magnet unit 10 includes a field magnet 11 that generates a static magnetic field B0 for the orientation of nuclear spins of samples or patients 100 in an acquisition area. The acquisition area is arranged in a patient tunnel 16 that extends in a longitudinal direction 2 through the magnet unit 10. A patient 100 may be moved into the acquisition area by the patient couch 30 and the positioning unit 36 of the patient couch 30. The field magnet 11 is normally a superconducting magnet that may provide magnetic fields with a magnetic flux density of up to 3T, or even higher in the latest devices. However, for lower field strengths it is also possible to use permanent magnets or electromagnets with normal-conducting coils.

Furthermore, the magnet unit 10 includes gradient coils 12 that are configured to superimpose variable magnetic fields in three spatial directions on the magnetic field B0 for the spatial differentiation of the captured imaging areas in the examination volume. The gradient coils 12 may be coils made of normal-conducting wires that may generate fields orthogonal to one another in the examination volume.

The magnet unit 10 likewise includes a body coil 14 that is configured to emit a radio-frequency signal supplied via a signal line 33 into the examination volume and to receive resonance signals emitted by the patient 100 and to deliver them via a signal line. However, the body coil 14 for the emission of the radio-frequency signal and/or receipt may be replaced by local coils 50 arranged in the patient tunnel 16 close to the patient 100. However, it is also conceivable for the local coil 50 to be configured to transmit and receive and therefore a body coil 14 may be omitted.

A control unit 20 supplies the magnet unit 10 with the different signals for the gradient coils 12 and the body coil 14 and evaluates the received signals. A controller 23 of the magnetic resonance tomography system 1 coordinates the subunits.

Thus, the control unit 20 includes a gradient control 21 that is configured to supply the gradient coils 12 via supply lines with variable currents that provide the desired gradient fields in the examination volume on a time-coordinated basis.

Furthermore, the control unit 20 includes a radio-frequency unit 22 that is configured to generate a radio-frequency pulse with a predefined time characteristic, amplitude and spectral power distribution for the excitation of a magnetic resonance of the nuclear spins in the patient 100. pulse powers in the kilowatt range may be achieved. The individual units are connected to one another via a signal bus 25.

The radio-frequency signal generated by the radio-frequency unit 22 is supplied to the body coil 14 via a signal connection and is emitted into the body of the patient 100 in order to excite the nuclear spins there. However, also conceivable is an emission of the radio-frequency signal via one or more local coils 50.

The local coil 50 then receives a magnetic resonance signal from the body of the patient 100, since because of the small spacing the signal-to-noise ratio (SNR) of the local coil 50 is better than on receipt by the body coil 14. The MR signal received by the local coil 50 is preprocessed in the local coil 50 and is forwarded to the radio-frequency unit 22 of the magnetic resonance tomography system 1 for evaluation and image capture. The signal connection 33 may be used for this, but a wireless transmission is also conceivable, for example.

The local coil 50 includes a device 60 with a field control material 70 that in the arrangement according to the application is located between the local coil 50 and the patient 100. The device 60 may for example be arranged inside or outside on a casing of the local coil 50, or may also be configured separately, so that the device 60 may be used with different local coils 50.

Figure 2:
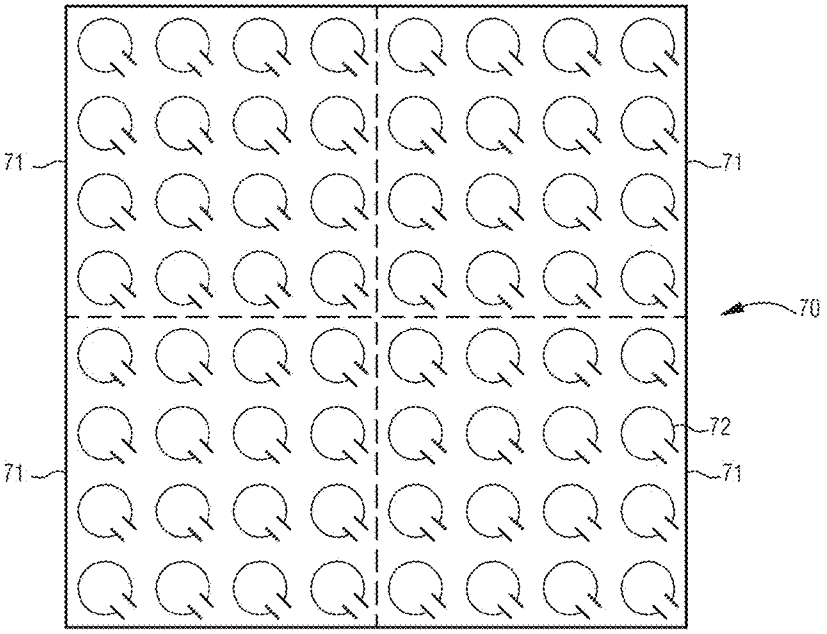
FIG. 2 depicts a schematic representation of a metamaterial according to an embodiment.

FIG. 2 depicts a schematic representation of a field control material 70 that may be used, in the form of a metamaterial. The metamaterial acts on the fields of the magnetic resonance signals. Hence it has small resonance elements 72 for electrical and/or magnetic alternating fields with the Larmor frequency. These may be provided for example, as shown schematically, by parallel resonant circuits that have an induction loop with a capacitor. The resonance elements 72 may be arranged in a regular grid. In order to be able to set different states of the field control material 70, it is conceivable for example for the capacitance to be provided by a PIN diode. Via a control connection, that is not shown in FIG. 2 for reasons of clarity, a variable voltage may be applied, that modifies the capacitance and thus the resonance frequency of the resonance element 72. For example, if the resonance frequency of the resonance element is set close to the Larmor frequency, the properties of the metamaterial change greatly as a function of the voltage. The properties are comparable to the refractive properties of optical materials, providing the resonance elements are significantly smaller than the wavelength of a radio wave with the Larmor frequency.

It is conceivable for the control connections to be connected together in groups, so that segments 71 arise in which the states of the metamaterial may be set independently of one another. By suitably distributing the segments and settings of the states, configurations corresponding to an optical lens may be provided, that focus the fields or waves, i.e. concentrate a sensitivity region of a local coil matrix on a side of the field control material 70 facing away from the patient 100 onto a predetermined volume. However, segments 71 may also be provided by physically separate elements of the field control material or metamaterial.

It is also conceivable for the metamaterial to have a plurality of slices stacked one above the other, as shown by way of example in FIG. 2.

The metamaterial with resonance elements 72 that may be electrically adjusted is also only one possibility for a field control material. Other materials or metamaterials are also known, whose properties may be controlled by the magnetic resonance tomography system 1.

Besides the aforementioned RF metamaterial using varactors or PIN diodes, other electrically adjustable materials such as liquid crystals, ferroelectric materials, magnetostrictive materials or electroactive polymers are conceivable.

Other field control materials are for example adjustable dielectrics. Adjustable dielectrics are materials that change their dielectric properties or permittivity in response to external influences such as electric fields, temperature or optical excitation. The respective microscopic mechanisms behind these properties depend on the respective material.

The field control material may for example have a negative refractive index for electrical and/or magnetic alternating fields with the Larmor frequency and thus effect a focusing of the sensitivity close to the local coil on the surface of the patient 100.

FIGS. 3*a* to 3*d* depict sensitivity regions 52 for a local coil 50 without a device 60 or with different states of the device 60.

Figure 3A:
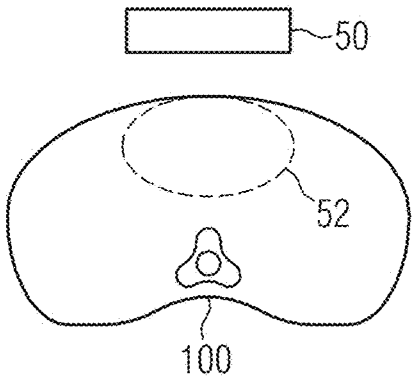
FIGS. 3A, 3B, 3C, and 3D depict sensitivity regions for a local coil with different states of the device according to an embodiment.

FIG. 3*a* first depicts a sensitivity region 52 for the local coil 50 on the patient 100. The characteristic of the sensitivity region 52 is shown by a line, on which a signal source with a constant field strength gives rise to an identical voltage or current in the local coil 50 or its antenna coils 51.

Figure 3B:
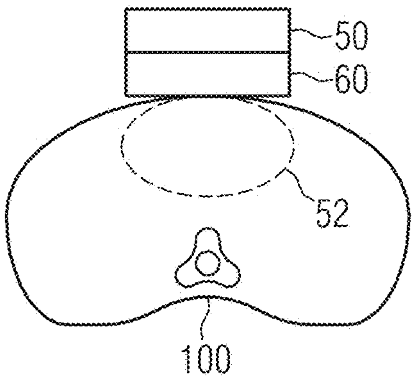

In FIG. 3*b* the device 60 with the field control material 70 is arranged in accordance with the application between the local coil 50 and the patient 100. In FIG. 3*b* the field control material 70 is in a first, transparent state, in which the sensitivity region 51 is substantially unchanged. There is for example a small change in the dielectric or permeable properties of a carrier material or the properties of the metamaterial without external influence. The sensitivity region 51 also depicts a field strength distribution when the antenna coil 51 is used as a transmitting antenna due to the reversibility of the electromagnetic waves. Thanks to the transparent state a field strength distribution that when transmitting with an unconnected local coil 50 is caused by the body coil may therefore also be anticipated. The transparent first state hence also enables the field strengths to be reliably determined for the SAR evaluation.

Figure 3C:
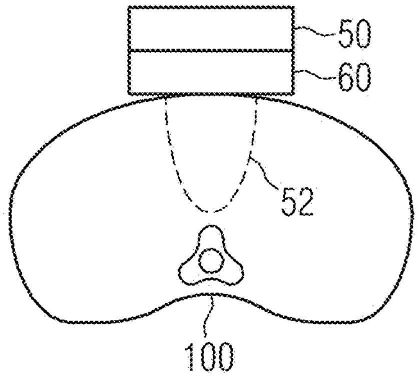

FIG. 3*c* depicts a sensitivity region 51 in a second state of the field control material 60. In this second state the sensitivity region 52 is narrower and reaches deeper into the interior of the patient 100. Such a sensitivity region may for example be achieved in that the field control material 70 is divided into separately activatable segments 71. This focusing may take place in two dimensions, so that the sensitivity region 71 is configured as wedge-shaped, or also in three dimensions if the peripheral segments 71 surround the central segment 71 in two dimensions, so that the sensitivity region 71 resembles a pointed cone or a lobe. Examples of the segmentation and activation are shown below in FIG. 4 and FIG. 5.

Figure 3D:
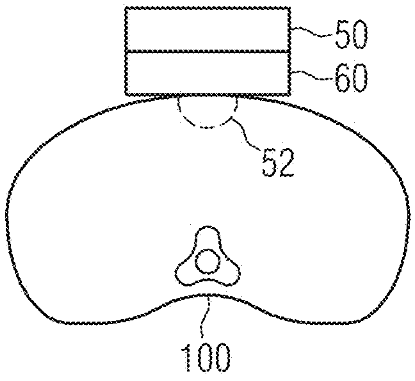

In contrast, FIG. 3*d* depicts a sensitivity region 71 that concentrates the sensitivity of the local coil 50 onto a region close to the local coil 50 on the surface of the patient 100. As already explained, this may be achieved for example by an activation that puts the metamaterial or field control material 70 into a state with a negative refractive index for electromagnetic waves with the Larmor frequency.

Figure 4:
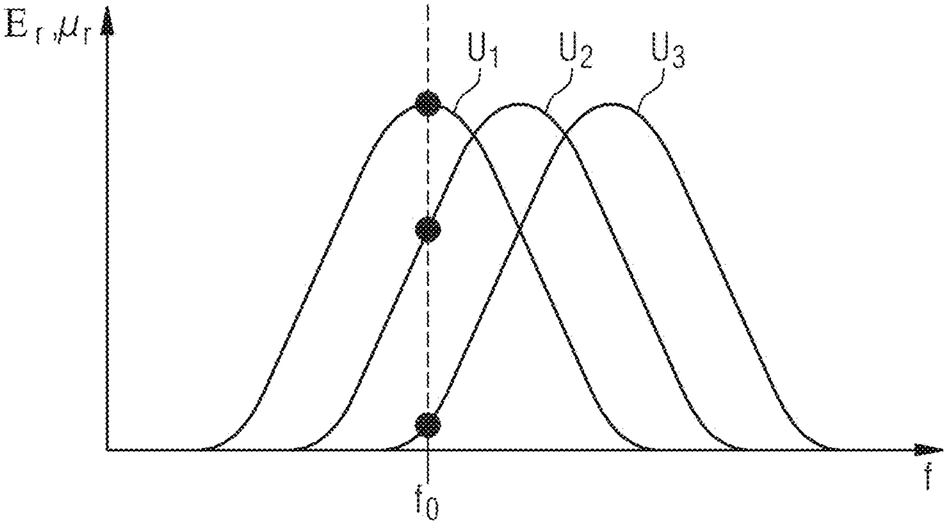
FIG. 4 depicts a relative dielectric constant or permeability for a metamaterial for use in the device according to an embodiment.

FIG. 4 schematically depicts the relative dielectric constant or permeability for a metamaterial with tunable resonance elements 72. The permeability $\mu_r$ or relative dielectric constant ER of the metamaterial is plotted on the ordinate; the frequency is plotted on the abscissa. The resonance curve shifts with different voltages (U1, U2, U3) applied to the variable capacitance. If the values of the permeability or dielectric constant for a constant frequency, for example a Larmor frequency, are considered, these change for this frequency with the voltage. Thus, the refractive index for an electromagnetic wave of a predetermined frequency, for example the Larmor frequency of the nuclear spins to be captured, may be modified with the voltage in the segment of the field control material 70. A matrix of segments 71 of the field control material 70 may then be shown as in FIG. 5 below.

Figure 5A:
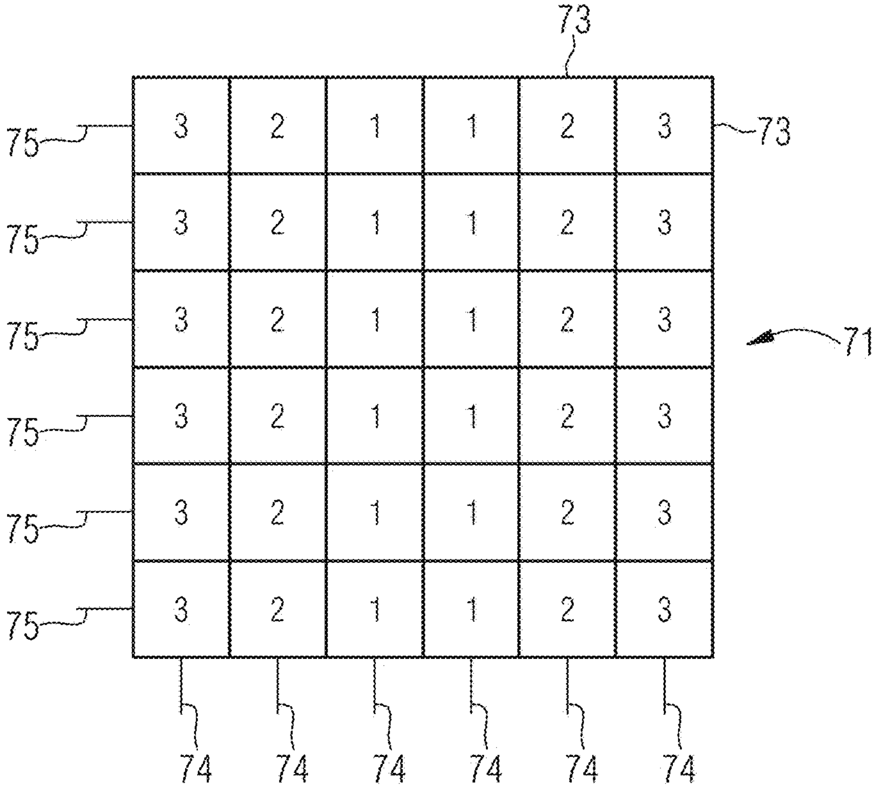
FIGS. 5A and 5B depict activation diagrams for segments of a field control material of a device according to an embodiment.

FIG. 5*a* depicts an activation diagram, in which two peripheral rows of segments 71 surround the intermediate rows of segments 71. In principle, the rows of segments may also be replaced by corresponding strips. The figures in the segments 71 indicate the intensity or levels of activation.

The activation may for example be a level of an applied voltage for the resonance elements 72 with varactors or PIN diodes as variable capacitances. The capacitance of a diode may also be varied with optical signals.

For variable dielectrics or materials with variable permeability it is also conceivable for the properties to be modified by voltages or applied electrical fields or in the case of optically active materials to be controlled by a level of illumination.

Figure 5B:
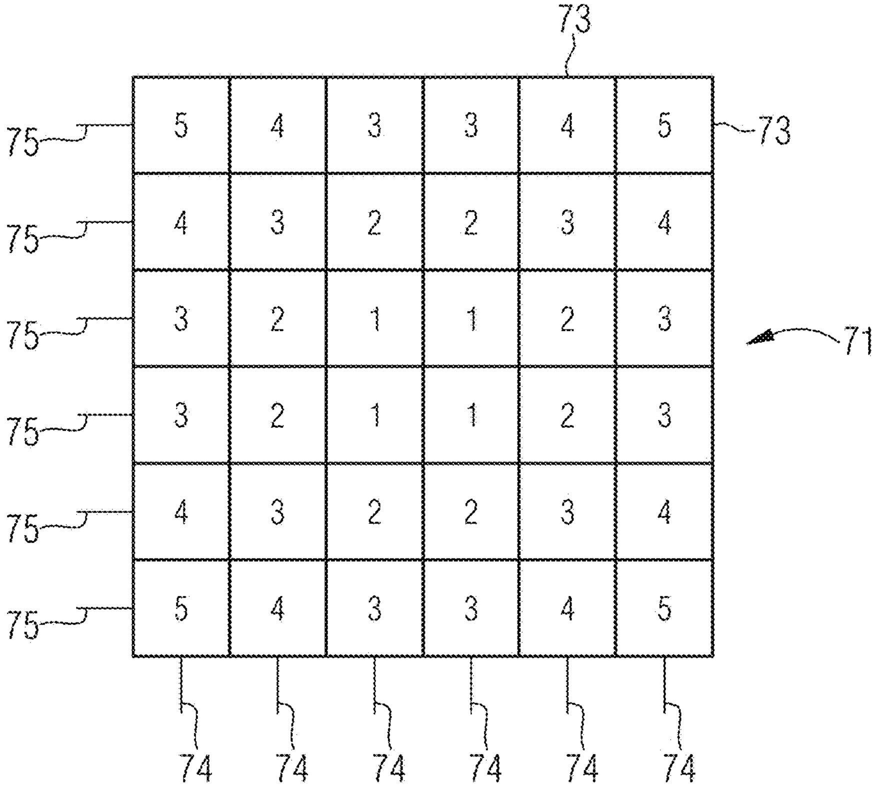

FIGS. 5A and 5B depict lines for column activation 74 and row activation, by which a pixel 73 of a segment 71 may be activated at an intersection of column activation 74 and row activation 75. It is conceivable for segment control to be provided for a segment 71 that for example receives a control command via a serial line, that is then converted into activation signals for column activation 74 and row activation 75 in order to reduce the number of lines.

Thanks to the predefined pattern, focusing of the alternating fields comparable to a cylinder magnifier arranged along the columns is achieved, so that the sensitivity region 72 is focused into the center.

In contrast, in FIG. 5*b* the pattern of the excitation is arranged rotationally symmetrically around the center point of the field control element. This also results in a rotationally symmetrical formation of the sensitivity region 52, comparable to a lobe, as shown in FIG. 3*c*.

It is also conceivable to swap the high activation values in the diagrams with the respective low activation values in FIGS. 4*a* and 4*b*. Correspondingly flattened, near-surface sensitivity regions 52 as shown in FIG. 3*d* may be achieved in this way.

The different sensitivity regions may for example be used, as shown in FIG. 3*d*, to focus the signal onto a near-surface slice in the patient 100 and thus to improve the SNR for images of these slices. It is also conceivable, thanks to wedge-shaped sensitivity regions as in FIG. 3*c*, to decouple adjacent slices of a parallel scan and in this way to accelerate the capture.

Figure 6:
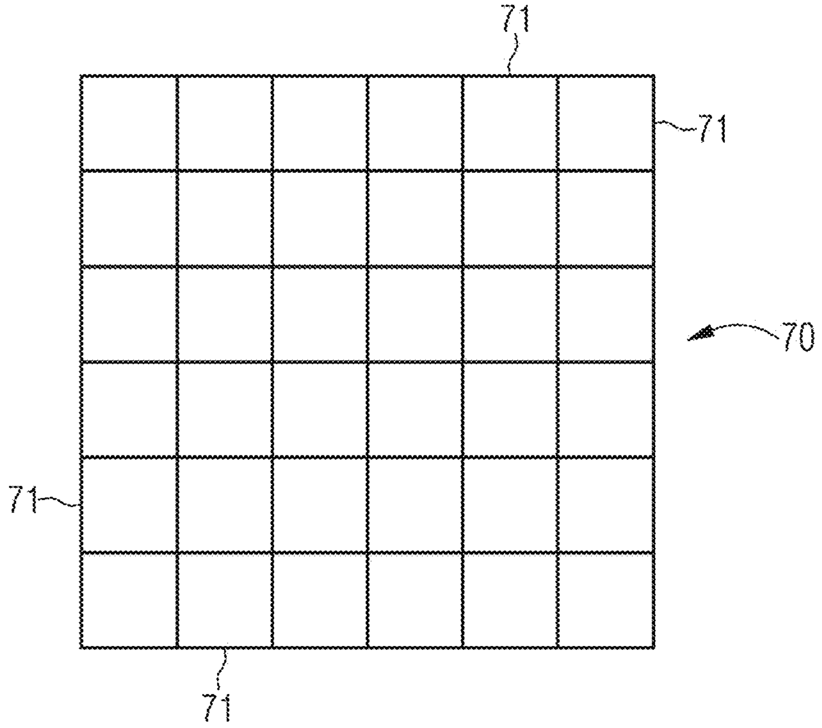
FIG. 6 depicts a field control material made up of a plurality of segments according to an embodiment.

FIG. 6 depicts by way of example how, as shown in FIGS. 5A and 5B, a field control material 70 may be extensively assembled from a plurality of segments 71. The individual segments 71 may be physically separate from one another and be assembled like a kind of tile to form the field control material 70. However, it is also conceivable for the subdivision into segments 71 and their subunit, pixels 73, to be merely logical due to the separate activatability of the subunit in the case of a one-piece segment 71 or field control material 70.

A segment may for example have dimensions comparable to those of an antenna coil 51 of an antenna matrix of the local coil 50 and be individually assigned thereto.

Figure 7:
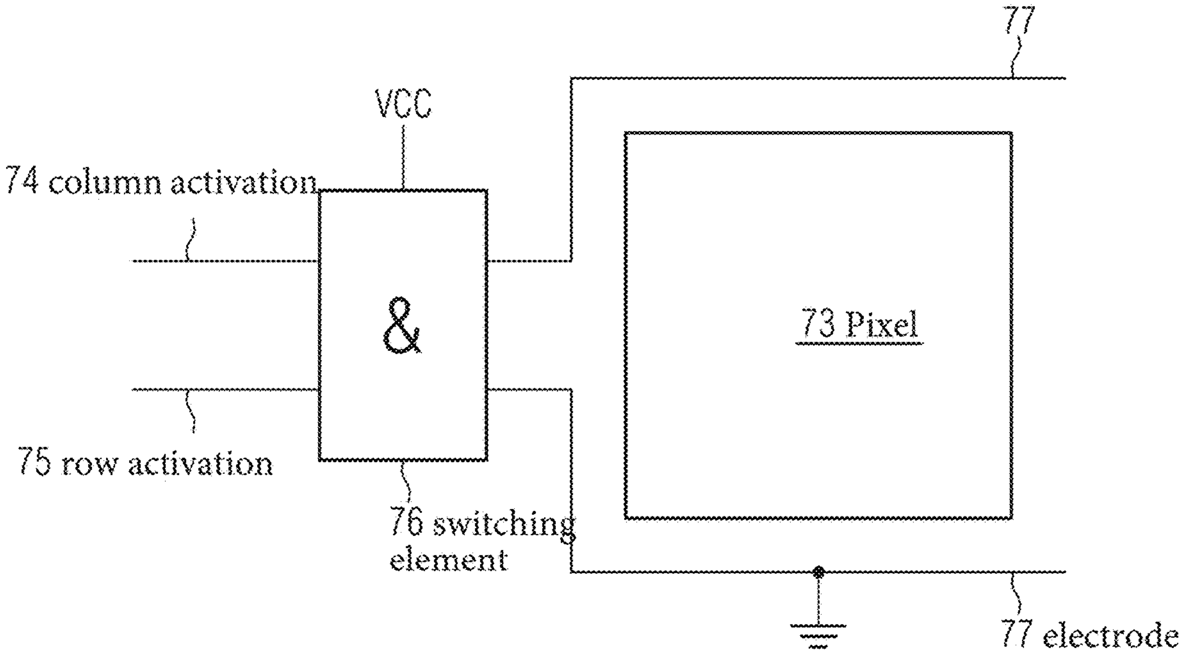
FIG. 7 schematically depicts an individual subunit of a segment according to an embodiment.

FIG. 7 in turn schematically depicts an individual subunit of a segment 71, that is referred to as a pixel 73. The pixel 73 may be an individual piece of a field control material 70 or else a section of an extensive piece of the field control material 70, for example of a segment 71 or of the whole field control material 70. The pixel 73 is then defined by the activation.

The activation in FIG. 7 is shown by way of example for a field-controlled pixel. Electrodes 77 are located above and below the pixel 73. At least one of the electrodes 77 is structured and defined by its lateral extension on the surface of the field control material 70, the pixel 73. The second electrode 77 may be configured as planar, for example as a ground electrode, or likewise structured, for example in order to be able to set the polarity of the voltage at a pixel independently.

A switching element 76 may be assigned to each pixel 73, and maintains the voltage at the electrodes 77 even if the individual pixel 73 is currently not set actively. It is for example conceivable for a setting value for a pixel 73 to be taken over by the switching element 76 if the signal to be set is not equal to 0 at one of column activation 74 and row activation 75 and a selection signal is present at the other. The lines and the switching element 76 may be arranged on one or both surfaces of the field control material 70. It is also conceivable that with a more complex switching element 76 a setting is also made via a common control line for all pixels 73 of the segment 71 or of the entire field control material 70.

Instead of the electrodes it is also conceivable in the case of an optically variable field control material 70 for the switching element 76 to activate a light source such as an LED or an OLED. Alternatively, a light intensity may also be achieved by light control elements such as LCD cells, comparable to an LCD matrix on the field control material 70, as may a planar illumination.

Figure 8A:
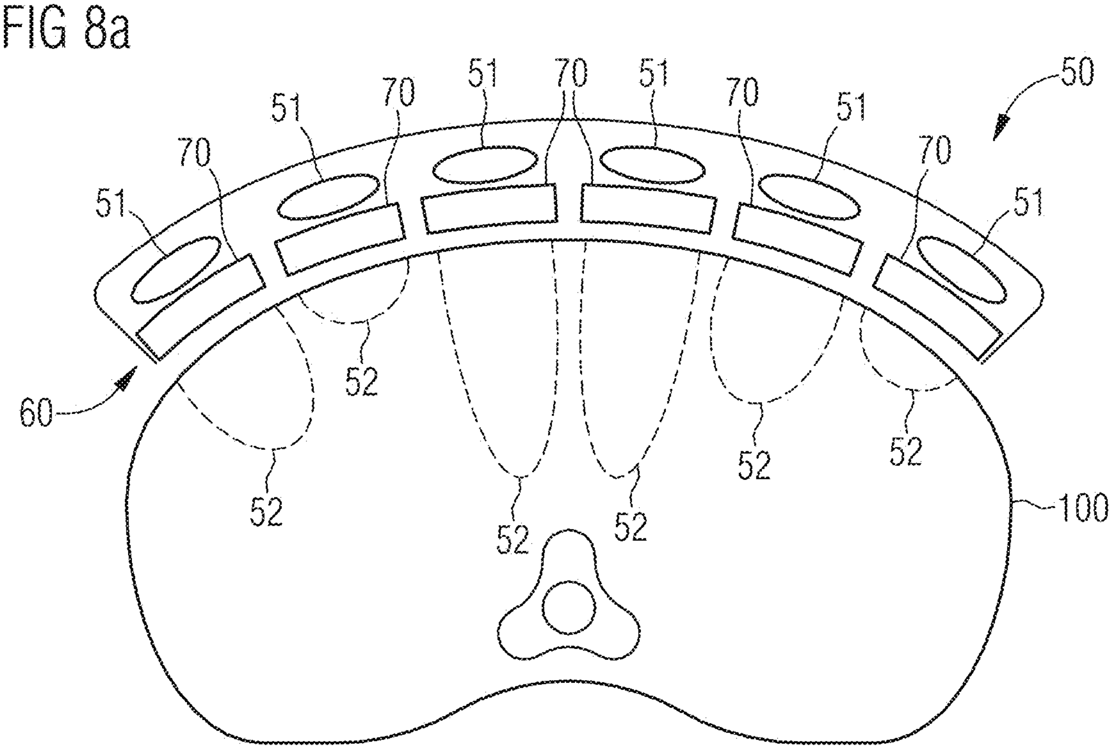
FIGS. 8A and 8B depict application examples of a local coil with the device according to an embodiment.
Figure 8B:
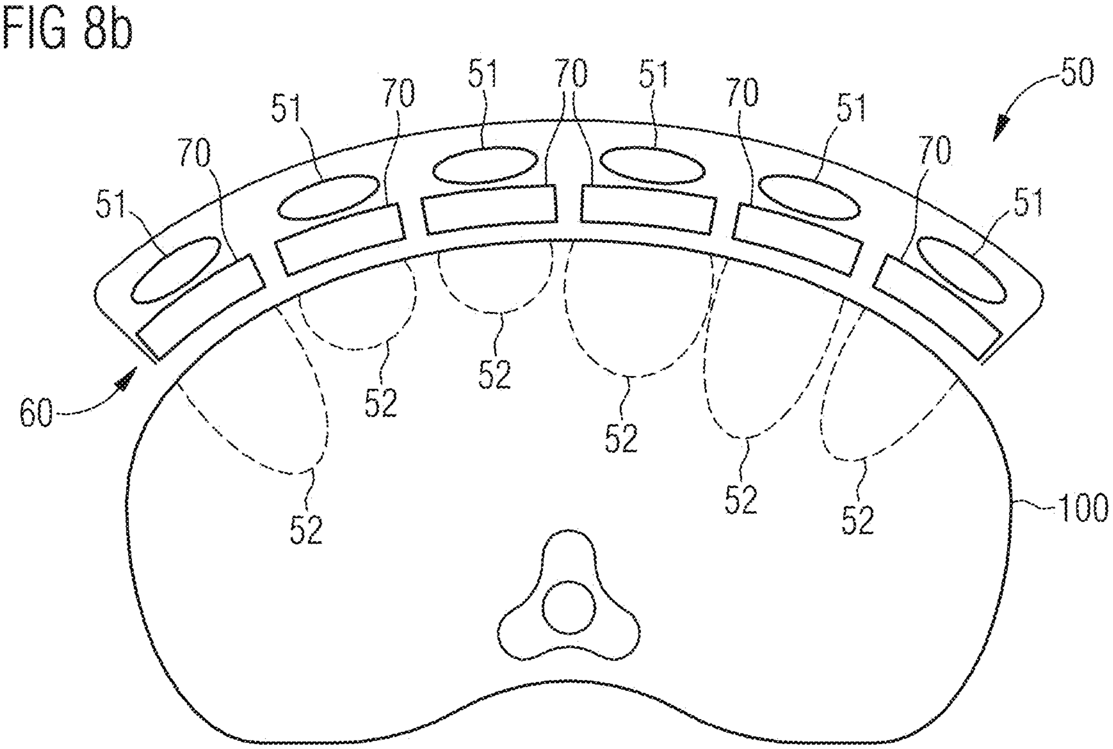

FIGS. 8A and 8B depict another application of the variable sensitivity regions 52, that are used for image capture by what is known as compressed sensing. In compressed sensing the volume to be mapped is scanned with different sensitivity patterns.

In FIGS. 8A and 8B a local coil 50 with a plurality of antenna coils 51 is arranged on the patient 100. A field control material 70 is arranged between the local coil 50 and the patient 100, either as part of the local coil 50, or as a separate device 60. The field control material 70 may be configured in one piece or may be arranged as shown in individual elements. What is important is that the sensitivity region 52 of an antenna coil 51 may be modified by a control signal to the field control material. Depending on the properties of the field control material 70 this change may be achieved by activation of the whole element made of field control material 70 under the antenna coil 51, or as in FIGS. 5A and 5B by different activation of segments 71 of the field control material 70, not shown individually in FIGS. 8A and 8B, between the antenna coil 51 and the patient 100.

FIGS. 8A and 8B here show by way of example two different scan patterns of the sensitivity regions 52. It is important that each volume element to be mapped is captured by different antenna coils with different sensitivity patterns. The patterns may be achieved by different activation of the segments 71, as explained for FIGS. 5A and 5B. The sensitivity patterns may be orthogonal to one another, so that the data necessary for an image reconstruction may be captured with as small as possible a number of scans.

The compressed sensing method may also advantageously be retrofitted for existing local coils 50 by a device 60 separate from the local coil 50.

Figure 9:
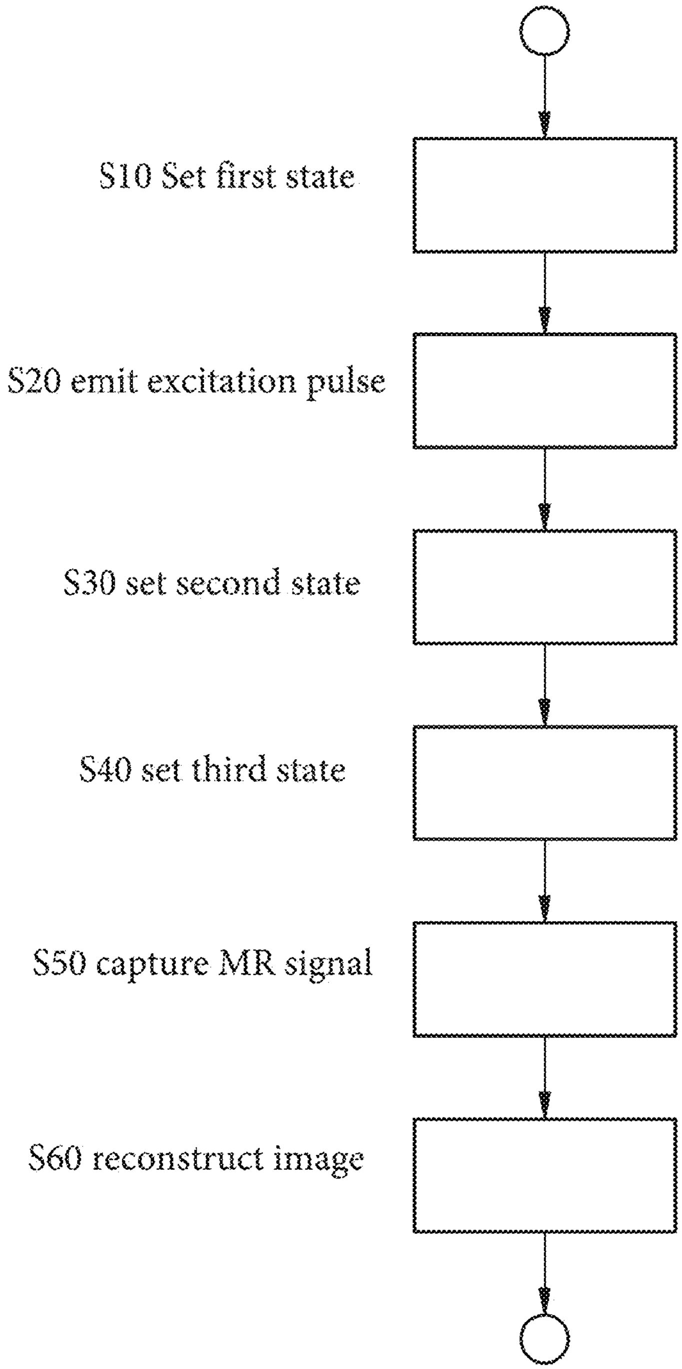
FIG. 9 depicts a schematic flow diagram of a method according to an embodiment.

FIG. 9 depicts a schematic flow diagram of a form of embodiment of the method.

In a step S20 the radio-frequency unit 22 emits an excitation pulse. This may be done for example via the body coil 14, or else via the local coil 50, if this is configured as a transmitting coil. The excitation pulse may be accompanied by other signals as part of a selected imaging sequence, for example of magnetic gradient fields, generated by the gradient control 21 with the gradient coils 12.

In a further step S30 the controller 30 sets a second state of the field control material 70. The second state is distinguished from a transparent state by different sensitivity regions 52. The state may for example be one of the sensitivity patterns explained in connection with FIG. 3. it is also conceivable for the local coil 50 to have a matrix of antenna coils 51 with elements or regions of the field control material 70 assigned to the antenna coils, as shown for example in FIGS. 8*a*, 8*b*, and for the controller 23 in each element or region of the field control material 70 to set a different second state differing from the transparent first state. This may for example be used as part of an image capture with compressed sensing, as explained for FIG. 8*a*, 8*b*, in order to scan the volume with different sensitivity patterns. However, an identical state of all regions or elements of the field control material 70 with the same relative sensitivity region for each antenna coil, for example as explained for FIG. 3*d*, is also conceivable, in order to improve the SNR during imaging of a near-surface volume.

In a step S50 the controller 23 then captures a magnetic resonance signal with the help of the radio-frequency unit 22 and the local coil 50 with the sensitivity pattern set in the second state of the field control material.

In a step S60 the controller 23 or a dedicated image reconstruction computer reconstructs an image from the magnetic resonance data. Steps S20, S30 and S50 with other settings may be repeated for this, for example with an excitation pulse with modified frequency, amplitude and or phase and/or with modified gradient fields, in order to ensure sufficient scanning in the k-space.

The reconstructed image may then for example be output on an output device to a user or may be further automatically evaluated.

In an embodiment of the method, in a step S10 prior to the emission of the excitation pulse in step S20, a first state of the field control material 70 is set by the controller 23, in which the field control material 70 is substantially transparent for the excitation pulse, for example its fields are not amplified or focused in a volume. In this way it may be ensured that the SAR limit values are also adhered to with the device 60, without having to change the excitation pulses or adjust the SAR monitoring.

In an embodiment of the method the step S20 of the emission of the excitation pulse is repeated; in other words, the nuclear spins are once again excited.

In a step S40 a third state of the field control material is set by the controller 23. The third state includes a different sensitivity region from the second state, for example however it is also not the transparent first state. With this modified sensitivity region, the controller 23 then captures magnetic resonance signals with the radio-frequency unit 22 and the local coil 50.

Further excitation pulses may be applied, further different states of the field control material 70 are set with further different sensitivity patterns and the magnetic resonance signals are captured with these different states. In this way the volume to be mapped is scanned with the same local coil in a different manner, this ultimately being used to reconstruct an image from these magnetic resonance signals using the compressed sensing method.

Imaging using compressed sensing may thus be used with an existing local coil 50 by the device 60.

In an embodiment of the method for operating a magnetic resonance tomography system (1) the field control material 70 is used to homogenize an excitation of the nuclear spins to be captured.

To this end it must first be determined how the excitation takes place without homogenization. This may be done for example by an excitation and measurement with the local coil with a phantom with a homogeneous nuclear spin distribution. the field control material 70 is not set or is not homogeneously set, so that the properties for the fields do not depend on the location in relation to the field control material. The excitation may be captured with a subsequent image and provided as a $B1^+$ map. The map may then be saved in the controller 23 for future image captures. The $B1^+$ map may then be provided by the controller 23 from the memory for an image capture.

In a further step a fourth state of the field control material 70 is determined by the controller 23 as a function of the $B1^+$ field map, so that the excitation is homogenized with a predetermined excitation pulse. The fourth state is therefore for example not equal to the first state, in which the field control material 70 is transparently or homogeneously configured. To this end, settings for the individual regions of the field control material 70 must homogenize the field strength in a region of the object under examination to be captured. For locations with a higher field strength a distribution or defocusing of the fields may be set, as already described for FIGS. 5A and 5B, whereas focusing is necessary for regions with a low field strength. The controller 23 may determine a fourth state by simulation of the fields in an optimization procedure subject to the constraint that a mean square deviation does not exceed a limit value.

However, it is also conceivable for a fourth state of the field control material 70 to be determined by the controller 23, in which the excitation fields are focused on a predetermined subregion of the object under examination or of the patient 100. This is also referred to as zoomed MRI, in which as it were the image capture zooms in on the subregion.

The determined fourth state in the field control material 70 is set by the controller 23 in a step S10, before the excitation pulse is emitted by the radio-frequency unit 22.

The further image capture takes place as already described for the other forms of embodiment.

It is to be understood that the elements and features recited in the appended claims may be combined in different ways to produce new claims that likewise fall within the scope of the present embodiments. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present embodiments have been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A device comprising:

a control input; and a field control material arranged between a local coil and a patient, wherein the field control material is configured to modify a spatial propagation of an electrical and/or a magnetic alternating field as a function of a control signal at the control input, wherein the field control material is configured, in a first state, to be transparent for the electrical and/or the magnetic alternating field, in a second state to raise a field strength of an incident electrical and/or magnetic wave front of an alternating field in a predetermined first volume relative to the first state, and in a third state to raise the field strength of an incident electrical and/or magnetic wave front of an alternating field in a predetermined second volume relative to the first state, wherein the predetermined second volume is different or disjunct from the predetermined first volume.

2. The device of claim 1, wherein the predetermined first volume and/or the predetermined second volume is a cone, a wedge, or a slice parallel to a surface of the device.

3. The device of claim 2, wherein the device is arranged on a surface of the local coil such that with an arrangement of the local coil, the device is arranged on a patient or on the surface thereof.

4. The device of claim 3, wherein the device further comprises a plurality of segments made of the field control material, wherein at least one segment of an antenna coil lies opposite a local coil matrix and each segment is configured to be transferred separately into the first state or the second state via the control input.

5. A magnetic resonance tomography system comprising:

a local coil comprising:

a local coil matrix; and a device comprising a control input and a field control material arranged between a local coil and a patient, wherein the field control material is configured to modify a spatial propagation of an electrical and/or a magnetic alternating field as a function of a control signal at the control input, wherein the field control material is configured, in a first state, to be transparent for the electrical and/or the magnetic alternating field and in a second state to raise a field strength of an incident electrical and/or magnetic wave front of an alternating field in a predetermined first volume relative to the first state, wherein the electrical and/or the magnetic alternating field has a frequency in a range of a Larmor frequency of nuclear spins to be mapped in the magnetic resonance tomography system;

wherein the device is arranged on a surface of the local coil such that with an arrangement of the local coil, the device is arranged on a patient or on the surface thereof; and a controller in signal connection with the control input of the device, wherein the controller is configured to set a state of the field control material as a function of a sequence.

6. The magnetic resonance tomography system of claim 5, wherein the controller is configured to transfer the field control material into the first state during an excitation pulse and into a second state during receipt of a magnetic resonance signal.

7. A method for operating a magnetic resonance tomography system, the magnetic resonance tomography system comprises a local coil and a controller, wherein the local coil comprises a local coil matrix and a device comprising a control input and a field control material arraigned between a local coil and a patient, wherein the field control material is configured to modify a spatial propagation of an electrical and/or a magnetic alternating field as a function of a control signal at the control input, wherein the field control material is configured, in a first state, to be transparent for the electrical and/or the magnetic alternating field, in a second state to raise a field strength of an incident electrical and/or magnetic wave front of an alternating field in a predetermined first volume relative to the first state, and in a third state, to raise the field strength of an incident electrical and/or magnetic wave front of an alternating field in a predetermined second volume relative to the first state, wherein the predetermined second volume is different or disjunct from the predetermined first volume, wherein the device is arranged on a surface of the local coil such that with an arrangement of the local coil, the device is arranged on a patient or on the surface thereof, wherein the controller is in signal connection with the control input of the device, wherein the controller is configured to set a state of the field control material as a function of a sequence, the method comprising:

setting, by the controller the first state of the field control material, outputting of an excitation pulse by a radio-frequency unit;

setting of the second state of the field control material by the controller;

capturing a magnetic resonance signal with the local coil, wherein outputting the excitation pulse is repeated, wherein the third state of the field control material is set by the controller and the magnetic resonance signal is in turn captured; and reconstructing of an image from the captured magnetic resonance signal;

output of the reconstructed image to a user.

8. The method of claim 7, wherein a plurality of sensitivity patterns is used for a parallelization on receipt of the magnetic resonance signal and/or also on output of the excitation pulses.

9. The method of claim 8, wherein the plurality of sensitivity patterns are orthogonal to one another, so that capturing and/or on output of the excitation pulses, data necessary for an image reconstruction may be captured with as small as possible a number of scans.

10. The method of claim 7, further comprising:

providing a $B1^+$ field map;

determining a fourth state of the field control material as a function of the $B1^+$ field map;

setting the fourth state of the field control material by the controller;

outputting a predetermined excitation pulse by the radio-frequency unit;

capturing the magnetic resonance signal with the local coil;

reconstructing the image from the captured magnetic resonance signal; and outputting the reconstructed image to the user.

* * * * *